US005191081A

United States Patent [19]
Parker

[11] Patent Number: 5,191,081
[45] Date of Patent: Mar. 2, 1993

[54] 1-CYANOMETHYL-4-CARBOXYMETHYL-3-KETOPIPERAZINE, SALTS THEREOF AND PROCESS FOR THEIR PREPARATION

[75] Inventor: Brian A. Parker, Nashua, N.H.

[73] Assignee: W. R. Grace & Co.-Conn., New York, N.Y.

[21] Appl. No.: 805,765

[22] Filed: Dec. 12, 1991

[51] Int. Cl.$^5$ ............................................. C07D 241/08
[52] U.S. Cl. ...................................... 544/384; 562/565
[58] Field of Search ......................................... 544/384

[56] References Cited

U.S. PATENT DOCUMENTS

| | | | |
|---|---|---|---|
| 3,313,779 | 4/1967 | White | 260/59 |
| 3,515,742 | 6/1970 | Morgan et al. | 260/465.5 |
| 3,733,355 | 5/1973 | Harris et al. | 260/534 E |
| 3,758,345 | 9/1973 | Popper et al. | 260/429 |
| 4,115,634 | 9/1978 | Bechara et al. | 521/126 |
| 4,190,571 | 2/1980 | Lai et al. | 544/384 |
| 4,704,465 | 11/1987 | Lannert et al. | 558/346 |

OTHER PUBLICATIONS

Berezowsky et al., *Can. J. Chem.* 48, pp. 163–175 (1970).
Kuehn et al., Chem. Abstracts v. 62,9129(d), 1965.
Blackmer et al., Chem. Abstracts v.71,18369c, 1969.
Badrinas Vancells, Chem. Abstracts v.92, 215062g, 1980.
White, Chem. Abstracts v.67, 22433d, 1967.
Abstract for JP59228 May 12, 1979.

Primary Examiner—Mukund J. Shah
Assistant Examiner—E. Bernhardt
Attorney, Agent, or Firm—Kevin S. Lemack; William L. Baker

[57] ABSTRACT

A novel intermediate useful in the synthesis of ethylenediaminetriacetic acid (ED3A) or its salts. N,N'-ethylenediaminediacetic acid (ED2AH$_2$) or a salt containing up to one equivalent of base cation is condensed with formaldehyde to form a stable 5-membered ring intermediate. The addition of cyanide across this cyclic material forms ethylenediamine N,N'-diacetic acid-N'-cyanomethyl or salts thereof (mononitrile-diacid), which is a useful intermediate in the production or ED3A. The nitrile in aqueous solutions may be spontaneously cyclized to form 2-oxo-1,4-piperazinediacetic acid (3KP) or salts thereof. In the presence of excess base, salts of ED3A are formed in excellent yield and purity.

1 Claim, No Drawings

1-CYANOMETHYL-4-CARBOXYMETHYL-3-KETOPIPERAZINE, SALTS THEREOF AND PROCESS FOR THEIR PREPARATION

BACKGROUND OF THE INVENTION

Ethylenediaminetriacetic acid (ED3A) or its salts (such as ED3ANa$_3$) has applications in the field of chelating chemistry, and may be used as a starting material in the preparation of strong chelating polymers, oil soluble chelants, surfactants and others. Conventional routes for the synthesis of ethylenediaminetriacetic acid were achieved via its N-benzyl derivative, which was subsequently hydrolyzed in alkaline solutions to ED3ANa$_3$, thus avoiding cyclization to its 2-oxo-1,4-piperazinediacetic acid (3KP) derivative. Syntheses attempted by both the alkaline condensation of chloroacetic acid with ethylenediamine, and the carboxymethylation of the diamine with formaldehyde and sodium cyanide resulted in complex mixtures requiring complex extraction techniques (e.g. almost exclusive solubility of 3KP in boiling dimethylformamide, Can. J. Chemistry 1970, 48(1), 163-175) to generate the desired product, and then in only relatively poor yield. In addition, conventional processes resulted in large quantities of by-product, such as ethylenediaminetetraacetic acid (ED4A). Where the by-products were especially objectionable, complicated blocking techniques were necessary in order to achieve a relatively pure solution.

One example of the synthesis of ethylenediamine-N,N,N'-triacetic acid is shown in *Chemical Abstracts* 78, Vol. 71, page 451, no. 18369c, 1969. There it is disclosed that ethylenediamine reacts with ClH$_2$CCO$_2$H in a 1:3 molar ratio in basic solution at 10° C. for 24 hours to form a mixture from which ethylenediamine-N,N,N'-triacetic acid can be separated by complexing the same with Co(III). The resulting cobalt complexes can be isolated through ion exchange.

The instant invention is directed to a novel composition of matter that is useful as an intermediate in the synthesis of ethylenediaminetriacetic acid or its salts in high conversions and excellent yield.

SUMMARY OF THE INVENTION

The problems of the prior art have been overcome by the instant invention, which provides a novel composition of matter useful as an intermediate in the synthesis of ethylenediaminetriacetic acid. Specifically, a mononitrile-monoacid is formed by reacting N,N'-ethylenediaminediacetic acid (ED2AH$_2$) or a salt thereof containing up to one equivalent of base cation with formaldehyde and water to form a hydroxymethyl derivative. The addition of cyanide forms 1-cyanomethyl-4-carboxymethyl-3-ketopiperazine or a salt thereof (the mononitrile-monoacid). This nitrile can be isolated in good yield in crystalline form. The addition of base will open this ring structure to form the salt of ED3A in excellent yield and purity.

DETAILED DESCRIPTION OF THE INVENTION

Suitable salts of ethylenediaminediacetic acid useful as the starting material in the instant invention include alkali and alkaline earth metal salts, in particular, the sodium and potassium salts. For purposes of illustration, the sodium salt will be used, although it should be understood that other salts may be employed without departing from the spirit and scope of the invention. One suitable reaction scheme for the synthesis of the mononitrilemonoacid is illustrated as follows:

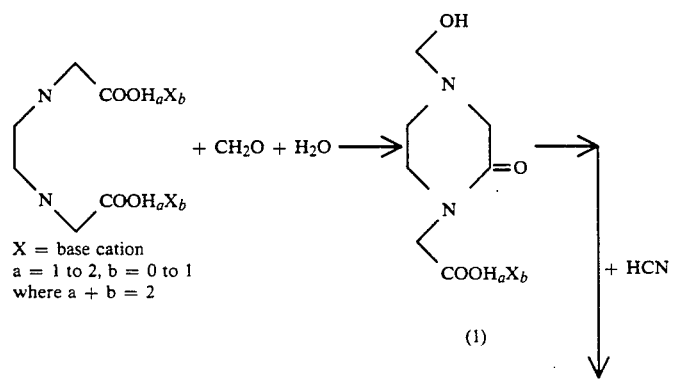

(1)

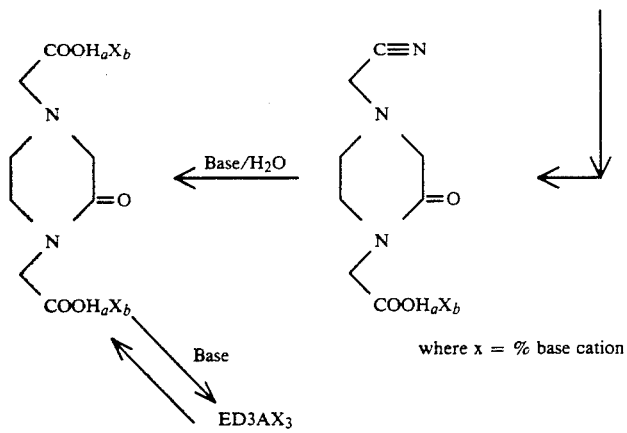

where x = % base cation

The starting material is ED2AH$_a$X$_b$, where X is a base, e.g., an alkali or alkaline earth metal, a is 1 to 2, and b is 0 to 1 in aqueous solutions. The reaction mixture also can be acidified with acids having pK$_a$'s less than or equal to 3, prior to during or after the addition of a cyanide source, to ensure complete formation of carboxymethyl-2-oxopiperazine (the lactam). Formaldehyde is added in stoichiometric amounts, although preferably it is added in a slight molar excess, preferably 0.5%-2.0%, essentially resulting in the hydroxymethyl derivative. Preferably the formaldehyde concentration is 55% or less in aqueous solution. Paraformaldehyde can also be used. The reaction proceeds quickly and forms readily at pH's geater than about 7.0. Preferably the temperature employed is about 0° to 65° C., most preferably about 15° to 65° C., although temperatures higher than 65° C. are operable.

Upon the addition of a cyanide source, 1-cyanomethyl-4-carboxymethyl-3-ketopiperazine or a salt thereof is formed, and can be isolated in good yield in crystalline form by conventional means after cooling the reaction mixture. Conversions are quantitative. The reaction should be conducted below the boiling point of the solution, preferably from about room temperature to about below the boiling point, most preferably about room temperature to about 70° C., to avoid the formation of impurities. Suitable sources of cyanide include gaseous hydrogen cyanide, an aqueous solution of hydrogen cyanide, or alkali metal cyanide such as sodium or potassium cyanide, etc. The cyanide may be used in stoichio-metric amounts, although slight molar excesses may be used, preferably 0.5%-2.0%.

Furthermore, in place of CH$_2$O and a cyanide source, HOCH$_2$CN, which is the reaction product of formaldehyde and cyanide, may also be employed in this method. Upon the addition of any suitable base or acid, this material may be hydrolyzed to 3KP. The addition of a base (>2.0 equivalents but preferably greater than or equal to 3.0 equivalents will open this ring structure to form the salt of ED3A. Heating the reaction mixture will enhance the rate of reaction.

The following procedure to obtain ED2AH$_2$ was for experimental purposes only. Far less elaborate schemes for the production of ED2AH$_2$ are possible. Any schemes known in the art can be employed for the production of ED2AH$_2$ and its salts, and the instant invention is not to be limited by any particular scheme.

The EDDAH$_2$ (98.20%) was obtained by acidification of EDDANa$_2$ to a pH of 5.50 with nitric acid, while maintaining the temperature of the solution <10° C. The resultant slurry was filtered by means of a Buchner funnel with the vacuum provided by a water aspirator. The filter cake was washed with approximately 7 liters of iced H$_2$O. To enhance drying, the cake was then washed with approximately 1 liter of MeOH. The crystals were then placed on 1 inch deep stainless steel trays, dried in a Stokes vacuum dryer, model 338F at 40° C. under a vacuum of 4 mm Hg, for 12 hours. Approximately 2 Kg of a white crystalline powder was recovered. Analysis of this powder showed it to be 98.2% ED2AH$_2$.

To form the compound of the instant invention, ED-2AH$_2$ was slurried with water in a 1 liter 5-necked round bottom flask equipped with a magnetic stirring bar, a condenser (ethylene glycol/H$_2$O @ 0° C.), A 0°-250° C. mercury thermometer, and a J-type thermocouple that provided a signal to a Love proportional controller, which maintained the temperature at the desired level. 37% CH$_2$O and 100% HCN were pumped at approximately 1 g/minute and 0.50 g/minute, respectively, buy an FMI micro metering pump at a setting of 0.5, via ⅛" Teflon tubing to the flask. No salts were present. It was found that the reaction proceeded as described above. The ED2AH$_2$, water and formaldehyde reacted to give the hydroxymethyl derivative of the lactam, which in turn reacted with HCN to give the cyclized mono-nitrile-monoacid. This solution was allowed to react overnight at 65° C. and one large peak was found on the chromatograms upon analysis by HPLC, which was later confirmed to be 1-cyanomethyl-4-carboxymethyl-3-ketopiperazine. The batch was then split in two. When the solution was cooled to <50° C., crystals precipitated which were subsequently isolated in approximately 70% yield. The other half of the batch was hydrolyzed with caustic (2:1 mole ratio, NaOH:EDDA), NH$_3$ was liberated, and it was found that 3KPNa$_2$ was the only product. This suggests the material was the mono-nitrilediacid. Final confirmation of this structure was successfully conducted by C$^{13}$ NMR. No attempts were made to enhance the recovery of the crystals, which is easily performed by concentration, pH adjustment, further cooling, etc.

An additional example was carried out in which 17.6 grams of ED2AH$_2$ was slurried in H$_2$O. The solution was heated to ~70° C. and 5.7 grams of glycolonitrile were added. Three samples were taken approximately 20 minutes apart. Analysis of these samples by HPLC showed a progressive increase in mononitrile monoacid, however it was not quantified.
What is claimed is:
1. A compound represented by the following formula:
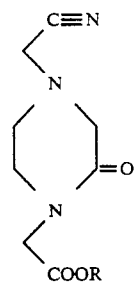
wherein R represents hydrogen or an alkali metal or alkaline earth metal.
* * * * *